(12) United States Patent
Yufa

(10) Patent No.: US 11,399,802 B2
(45) Date of Patent: Aug. 2, 2022

(54) METHODS AND ULTRASOUND APPARATUS

(71) Applicant: Ann Rachel Yufa, Colton, CA (US)

(72) Inventor: Ann Rachel Yufa, Colton, CA (US)

( * ) Notice: Subject to any disclaimer, the term of this patent is extended or adjusted under 35 U.S.C. 154(b) by 0 days.

(21) Appl. No.: 16/873,715

(22) Filed: Jun. 10, 2020

(65) Prior Publication Data

US 2021/0386400 A1 Dec. 16, 2021

(51) Int. Cl.
*A61B 8/00* (2006.01)
*B06B 1/06* (2006.01)

(52) U.S. Cl.
CPC ............ *A61B 8/4472* (2013.01); *A61B 8/461* (2013.01); *A61B 8/565* (2013.01); *B06B 1/0607* (2013.01); *A61B 2560/0214* (2013.01); *A61B 2562/222* (2013.01)

(58) Field of Classification Search
CPC ...... A61B 2560/0214; A61B 2562/222; A61B 8/4472; A61B 8/461; A61B 8/565; A61B 8/56; B06B 1/0607; B06B 1/0207; B06B 1/0622; B06B 2201/40; G01S 7/5208; G01S 7/52084; G01S 7/52096
See application file for complete search history.

(56) References Cited

U.S. PATENT DOCUMENTS

| | | | |
|---|---|---|---|
| 6,251,073 B1 * | 6/2001 | Imran | A61B 8/4209 600/443 |
| 9,402,599 B2 | 8/2016 | Okuda | |
| 9,402,601 B1 | 8/2016 | Berger et al. | |
| 9,408,589 B2 | 8/2016 | Ko et al. | |
| 9,427,209 B2 | 8/2016 | Okuda | |
| 9,445,788 B2 | 9/2016 | Kumazawa | |
| 9,476,861 B2 | 10/2016 | Takenaka et al. | |
| 2011/0125063 A1 * | 5/2011 | Shalon | A61B 5/4205 600/590 |
| 2015/0032300 A1 * | 1/2015 | Arethens | G06F 11/1645 701/17 |
| 2016/0317131 A1 * | 11/2016 | Schwartz Klessel | A61B 8/4472 |

OTHER PUBLICATIONS

{http://www.lumify.philips.com/Web/?origin=%7 ... } (see Specification).
{http://www.thesun.co.uk/news/2101180/next-year ... } (see Specification).

* cited by examiner

*Primary Examiner* — Yi-Shan Yang
*Assistant Examiner* — Alexei Bykhovski

(57) ABSTRACT

This invention is the improved methods and ultrasound apparatus with the wirelessly chargeable battery of the ultrasound probe and with the record of the ultrasound data and ultrasound images on the removable memory card. The improved methods provide the steps of the operation of the improved ultrasound apparatus, and the improved ultrasound apparatus includes the microprocessor unit and control organs unit, which provide control of an ultrasound unit, comprising piezoelectric devices, a transmission unit, a battery unit, including battery and battery wireless charging control circuitry, indication unit, and includes a card insertion registration device recognizing the presence of a removable memory card in the ultrasound probe.

10 Claims, 4 Drawing Sheets

METHODS AND ULTRASOUND APPARATUS

FIELD OF THE INVENTION

The invention relates to the methods and ultrasound apparatus. More specifically, invention relates to the medical ultrasound diagnostic apparatus with the ultrasound probe providing the wireless charging of the chargeable battery and wireless communication with the operator's/doctor's/patient's Smart Device (Smart Phone, iPad, iPhone, etc.) and with the record of ultrasound data and/or ultrasound images on the removable memory card of the ultrasound probe or on the removable memory card of Smart Device.

BACKGROUND OF THE INVENTION

There are known many methods and ultrasound diagnostic apparatus (devices) using ultrasound images in the medical field.

Ultrasound allows to examine inside of a medical subject (e.g.: human or animal bodies) externally (non-destructively and non-harmlessly). It has been applied in various fields such as inner defect examination, disease diagnosis and alike.

Generally, the ultrasound diagnostic apparatus includes an ultrasound probe [hereinafter may be referred to as "probe"] and a central station (central unit). The probe transmits ultrasonic waves toward a medical subject [hereinafter may be referred to as "subject" or "diagnostic subject"] and receives ultrasonic echoes from the subject, and the central unit electrically/electronically processes the acquired signals to generate an ultrasound image. Ultrasound is applied to an ultrasound diagnostic imaging apparatus which visualizes the inner condition of a medical subject on the basis of a received signal generated from reflection ultrasound from inside of the medical subject by scanning inside the medical subject with ultrasound. Such ultrasound diagnostic imaging apparatus is provided with an ultrasound probe which transmits and receives ultrasound to and from a medical subject.

Commonly, ultrasound probe is provided with a plurality of piezoelectric devices each of which generates ultrasound by vibrating mechanically based on a driving signal and generates a received signal by receiving reflection ultrasound caused by the acoustic impedance difference in the subject by utilizing the piezoelectric phenomena.

Even in the recently issued patents, the ultrasound diagnostic apparatuses use the electrical cables for communication between the probe and central unit and/or use the cables for charging battery in the wirelessly communicating probes.

For example, the ultrasound probe and ultrasound diagnostic imaging apparatus by U.S. Pat. Nos. 9,402,599 and 9,427,209 uses electrical cable for communications between probe and central unit. Specifically, the cable electrically connects the probe and central unit. This ultrasound diagnostic imaging apparatus generally includes a central unit (an ultrasound diagnostic imaging apparatus "main body") and an ultrasound probe. The ultrasound probe of that invention transmits ultrasound to a diagnostic subject and receives reflection wave/echo from the subject. The central unit sends by cable (wire) a drive signal to the probe and visualizes, as an ultrasound image of the inside condition of the medical subject, on the basis of a received electrical signal generated by the ultrasound probe. The ultrasound probe is provided with transducers formed of a plurality of piezoelectric device(s)

The central unit includes an operation input device, a transmitting device, a receiving device, an image generation device, a memory, a digital scan converter, a display and a control device. The operation input device includes various types of control organs: switches, buttons, a trackball, a mouse, a key board and alike in order to provide the commands, for example such as: turn-on/turn-off the ultrasound diagnostic apparatus, start/stop of diagnosis, and the operation input device outputs operation signals to the control device.

The control is provided only from the central station/unit having the control organs. The communication between central station and probe by a cable create a significant limitation of the probe mobility and operator's inconvenience, as a result of such limitation. The apparatus by this invention does not provide: the possibility to use the Smart Devices (e.g., such as Smart Phone, iPad, iPhone, etc.); the secured prevention of the patient's medical ultrasound information/images record on the removable memory card (hereinafter may be referred to as "card"); and does not provide the battery wireless charging circuitry [hereinafter the "battery" may be referred to as "regular non-chargeable battery" or "chargeable by cable battery" (battery chargeable by cable) or "wirelessly chargeable battery"].

The ultrasound image diagnosis apparatus by U.S. Pat. No. 9,408,589 generally includes an ultrasonic transducer, an ultrasonic probe, and an ultrasound image diagnosis apparatus (central station/unit). The probe include a plurality of piezoelectric elements arranged in at least one column; individual electrodes provided on at least one surface of top and bottom surfaces of each of the piezoelectric elements; side electrodes extending toward one side surfaces of the piezoelectric elements from the individual electrodes; and a side electrode substrate including wiring lines that are bonded to the one side surfaces of the piezoelectric elements and are electrically connected to the side electrodes, respectively. The central unit is analogically connected to the probe by the electrical cable too.

This device has the same deficiency, i.e.: the cable create the same significant limitation of the probe mobility and operator's inconvenience, as a result of such limitation, and the device also does not provide: the possibility to use the Smart Devices (e.g., such as Smart Phone, iPad, iPhone, etc.); the secured prevention of the patient's medical ultrasound information/images record on the removable memory card; and does not provide the battery wireless charging circuitry.

Another ultrasound image diagnosis apparatus by U.S. Pat. No. 9,445,788 generally includes a head unit (probe) formed by arraying a plurality of ultrasound transducing elements one-dimensionally or two-dimensionally. Each of the ultrasound transducing elements is connected to the connector through a signal line provided in the cable. Thus, the communication of the central unit (main unit) with the probe (head unit) is also provided by the electrical cable. This ultrasound probe includes a plurality of channels in parallel, each comprising ultrasound transducing element, and a signal line. The main unit includes a transmitting unit, a receiving unit, a measuring unit, a display processing unit, a navigation processing unit, a control unit, and a medical diagnosing unit. The transmitting unit transmits excitation signals for exciting the ultrasound transducing elements. The receiving unit receives the signals received by the ultrasound transducing elements, and outputs the received signals. The measuring unit measures the feature values of the signals output from the receiving unit. A feature value includes, for example, the time required between transmitting an ultrasound wave and receiving the reflected ultrasound wave. The measuring unit outputs measurement information indicating the measured feature values to the storage medium unit, interface unit, display processing unit, navigation processing unit, or to control unit under the control of the control unit. The storage medium is a semiconductor memory. The storage medium stores various kinds of information such as the above measurement information. The interface unit performs communication processing conforming to the USB standard. The display processing unit generates an image signal for causing the monitor to display an image on the basis of the above measurement information, supplied from the control unit. The navigation processing unit comprises a microprocessor. The control unit comprises another microprocessor. The medical diagnosing unit also includes an imaging control unit, image generating unit, that massive memory unit, and display unit.

This device has also inherited the same deficiency, such as the electrical cable, creating the same significant limitation of the probe mobility and operator's inconvenience, as a result of such limitation. This patented apparatus in the same manner does not provide: the possibility to use the Smart Devices (e.g., such as Smart Phone, iPad, iPhone, etc.); and does not provide the battery wireless charging circuitry.

There are known many other ultrasound apparatus providing cable communication between central station and ultrasound probe. For example, the ultrasound diagnostic device by U.S. Pat. No. 9,476,861 and ultrasound diagnostic device described in: "Philips Lumify Portable Ultrasound Machine" includes an ultrasound probe which already communicates with the central unit represented by a Smart Device, but the communication is still provided by an electrical cable.

These devices, communicating via wire (cable), have the same deficiency, such as the electrical cable, which creates the same significant limitation of the probe mobility and operator's inconvenience, as a result of such limitation, and the "Philips Lumify Portable Ultrasound Machine" does not prevent the secured patient's medical ultrasound information/images record on the removable memory card, and does not provide the wireless charging circuitry for ultrasound probe's battery [for example, such wireless charging circuitry as known for "iPhone8".

The control of the imaging procedure by ultrasound probe, communicating with the host computer (central station/unit) by cable (wire) [for example, by standard high speed serial bus] or wirelessly: by infrared link or by radio frequency, is described in the U.S. Pat. No. 9,402,601. Referring to the description, the hand-held ultrasound system includes integrated electronics, including control circuitry, beamforming and circuitry transducer drive circuitry. The electronics communicate with a host computer (central station/unit) using an industry standard high speed serial bus. The ultrasonic imaging system is operable on a standard, commercially available, user computing device without specific hardware modifications, and is adapted to interface with an external application without modification to the ultrasonic imaging system to allow a user to gather ultrasonic data on a standard user computing device such as a personal computer.

Additionally, the system may provide the wireless communication with the host computer by infrared link as defined by the Infrared Data Association or utilizing Bluetooth technology.

This device has the same deficiency, such as the electrical cable, creating the same significant limitation of the probe mobility and operator's inconvenience, as a result of such limitation, if the electrical cable is used, and does not provide the secured prevention of the patient's medical ultrasound information/images record on the removable memory card, if the Smart Devices (e.g., such as Smart Phone, iPad, iPhone, etc.) are used, and does not provides the battery wireless charging circuitry.

Another known ultrasound diagnostic apparatus includes an ultrasound probe wirelessly communicating with the Smart Device.

This device does not prevent the secured patient's medical ultrasound information/images record on the removable memory card, and does not provide the battery wireless charging circuitry.

Those skilled in the art will readily observe that numerous modifications and advantages of the improved methods and ultrasound apparatus with the wirelessly chargeable battery of the ultrasound probe and with the record of the ultrasound data/images on the removable memory card may be made while retaining the teachings of the invention.

The saving of the patient's ultrasound data/images on the Smart Device's regular memory is prohibited by the patient's medical information privacy privilege, therefore, the removable memory card will be extremely efficient instrument for using modern Smart Device technology (e.g. such as Smart Phone, iPad, iPhone, etc.) in the field of ultrasound diagnosis. Keeping patient's ultrasound diagnostic images, as a private, on the removable memory card but not on the openly wirelessly accessible Smart Device provides a secured convenience for medical organizations and doctors. The removable memory card can be kept in the doctor's archived patient's file or erased after the data/images from the card will be transmitted to (recorded in) the patient's electronic file.

The implementation of the wireless charging devices in the procedures of the medical ultrasound diagnosis provides complete mobility of the ultrasound diagnostic probe, as well as doctor's/operator's independence on the patient's location (e.g., for the emergency patients in the wild mountain forests areas, in the rural Alaskan or other difficult to approach areas, etc.)

Thus, the known prior art does not provide the efficient, secured and convenient methods and ultrasound apparatus with the wirelessly chargeable battery of the ultrasound probe, and with the record of the ultrasound data and images on the removable memory card of the ultrasound probe or on the removable memory card of Smart Device (e.g., on Smart Phone, on iPad, on iPhone or on the other suitable portable devices, etc.), and the present invention substantially departs from the devices of the prior art.

DESCRIPTION OF THE DRAWING

In order that the invention and the manner in which it is to be performed can be more clearly understood, embodiments thereof will be described by way of example with reference to the attached flowcharts and drawings, of which.

Figure 1:
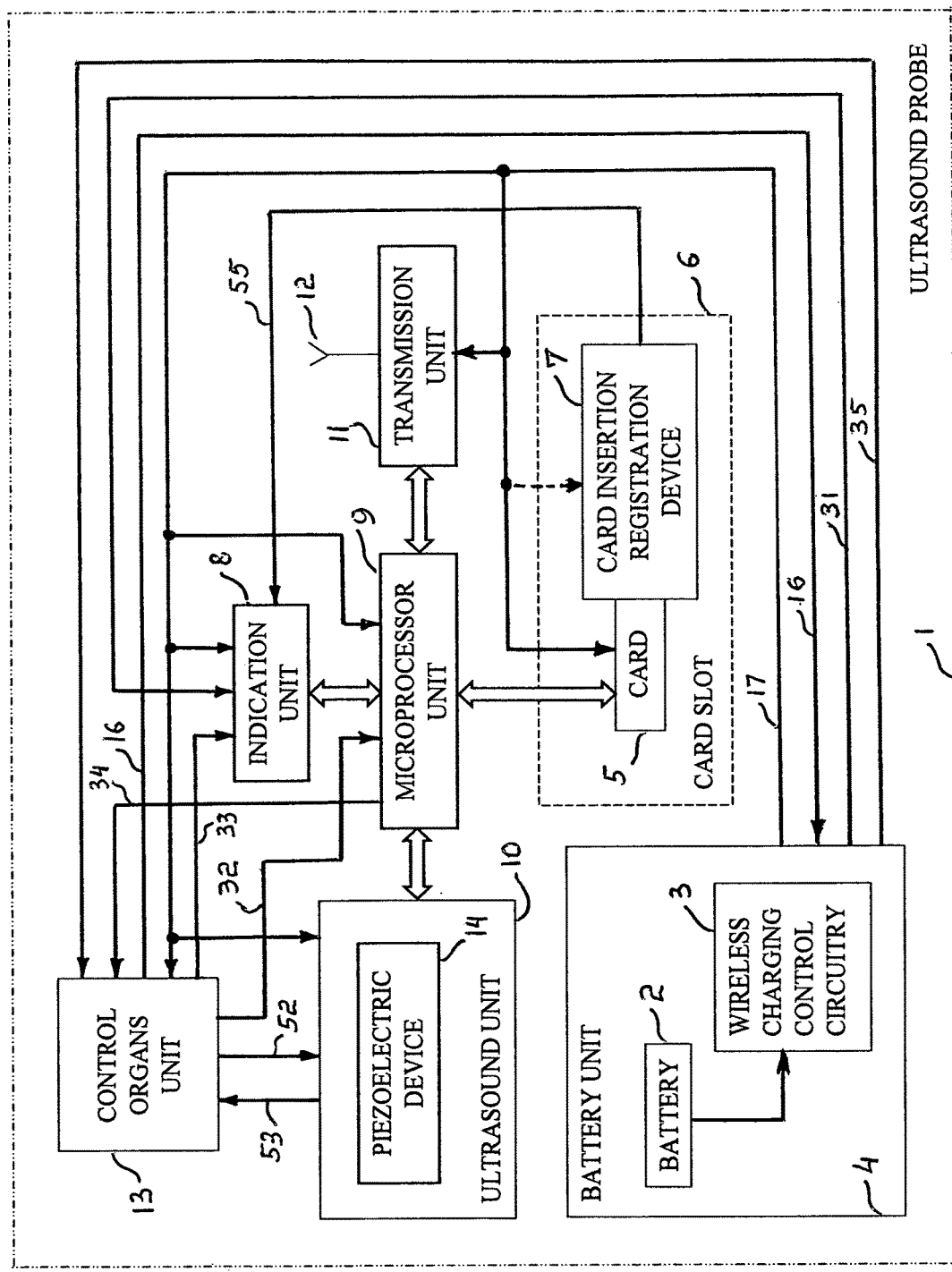
FIG. 1 is a simplified drawing (block-diagram) of the improved ultrasound probe.

It is understood, that these illustrations and drawings are the examples of the improved methods and apparatus configurations and architectures, and those skilled in the art will readily observe that numerous steps, structures, modifications and advantages of the improved methods and ultrasound apparatus (i.e., ultrasound probe with the wirelessly chargeable battery and with the record of the ultrasound data and images on the removable memory card) may be made while retaining the teachings of the present invention.

SUMMARY OF THE INVENTION

In view of the foregoing disadvantages inherent in the known prior art, the present invention provides an improved methods and ultrasound apparatus with the wirelessly chargeable battery of the ultrasound probe and with the record of the ultrasound data/images on the removable memory card of the ultrasound probe or on the removable memory card of Smart Device (e.g., on Smart Phone, on iPad, on iPhone, etc.). As such, the general purpose of the present invention, which will be described hereinafter in greater details, is to provide the improved methods and wirelessly chargeable ultrasound probe with the record of the ultrasound data/images on the removable memory card. The improved methods and apparatus have many of the advantages of the wireless charging of the ultrasound probe and recording of the ultrasound data/images on the removable memory card mentioned hereinabove and mostly heretofore, and many novel features that result in the efficient, secured and convenient methods and ultrasound apparatus with the wirelessly chargeable battery of the ultrasound probe and with the record of the ultrasound data/images on the removable memory card, which is not anticipated, rendered obvious, suggested or even implied by any of prior art methods and apparatus/devices for ultrasound probes, either alone or in any combination thereof.

This invention, methods and ultrasound apparatus with the wirelessly chargeable battery of the ultrasound probe and with the record of the ultrasound data/images on the removable memory card, provides the secure saving of the patient's ultrasound data/images on the removable memory card, which is extremely efficient instrument for using modern Smart Device technology (e.g. such as Smart Phone, iPad, iPhone, etc.) in the field of ultrasound diagnostic. Keeping patient's ultrasound diagnostic images, as a private, on the removable memory card provides a secured convenience for medical organizations and doctors. The removable memory card can be kept in the doctor's archived patient's file or erased after the data/images from the card will be transmitted to (recorded in) the patient's electronic file. The wireless charging of the wireless communicating ultrasound probe provides the unlimited mobility of the ultrasound diagnostic apparatus (ultrasound probe), for example, for the patients located at the difficult accessible areas (e.g., the emergency patients in the wild mountain forests areas, in the rural and wild Alaskan or other difficult to approach areas, etc.).

To attain this, the present invention generally comprises ultrasound unit, including piezoelectric devices, and transmission unit, which are controlled by the microprocessor unit and by control organs unit. Also, comprises a battery unit, including battery and wireless charging control circuitry, and comprises a card insertion registration device recognizing the presence of the removable memory card in the ultrasound probe. Additionally, the present invention comprises the wirelessly chargeable battery providing unconditional advantage for mobility of the ultrasound probe.

DESCRIPTION OF THE PREFERRED EMBODIMENTS

With reference now to the algorithms and drawings, an improved methods and ultrasound apparatus with the wirelessly chargeable battery of the ultrasound probe and with the record of the ultrasound data/images on the removable memory card embodying the principles and concepts of the present invention.

As it has been mentioned hereinabove with respect to term of "Smart Device" (e.g. such as Smart Phone, iPad, iPhone, etc.), the term "removable memory card", hereinabove and hereinbellow solely and/or jointly accumulate (in the same manner as for Smart Device) the meanings of the "removable card", "memory card", "card" and/or any other removable (portable) memory, etc. The term "probe", hereinabove and hereinbellow solely and/or jointly accumulate the meanings of the "ultrasound probe", "medical ultrasound probe" and/or any other ultrasound sensors (probes), etc. used in the medical diagnostic procedures. The term "chargeable" accumulate the mining of the "rechargeable", etc. Therefore, the use at least one of the terms does not exclude the other meanings for the used terms, if otherwise not specified. This description (drawings, specification and claims) has many other terms for which this condition is applicable too.

In the FIG. 1 is shown the simplified block-diagram of the improved ultrasound probe 1. The probe 1 comprises a battery 2. The battery 2 can be a non-chargeable replaceable battery or a chargeable battery. The battery 2 is connected to the wireless charging control unit 3 of the battery unit 4.

Figure 2:
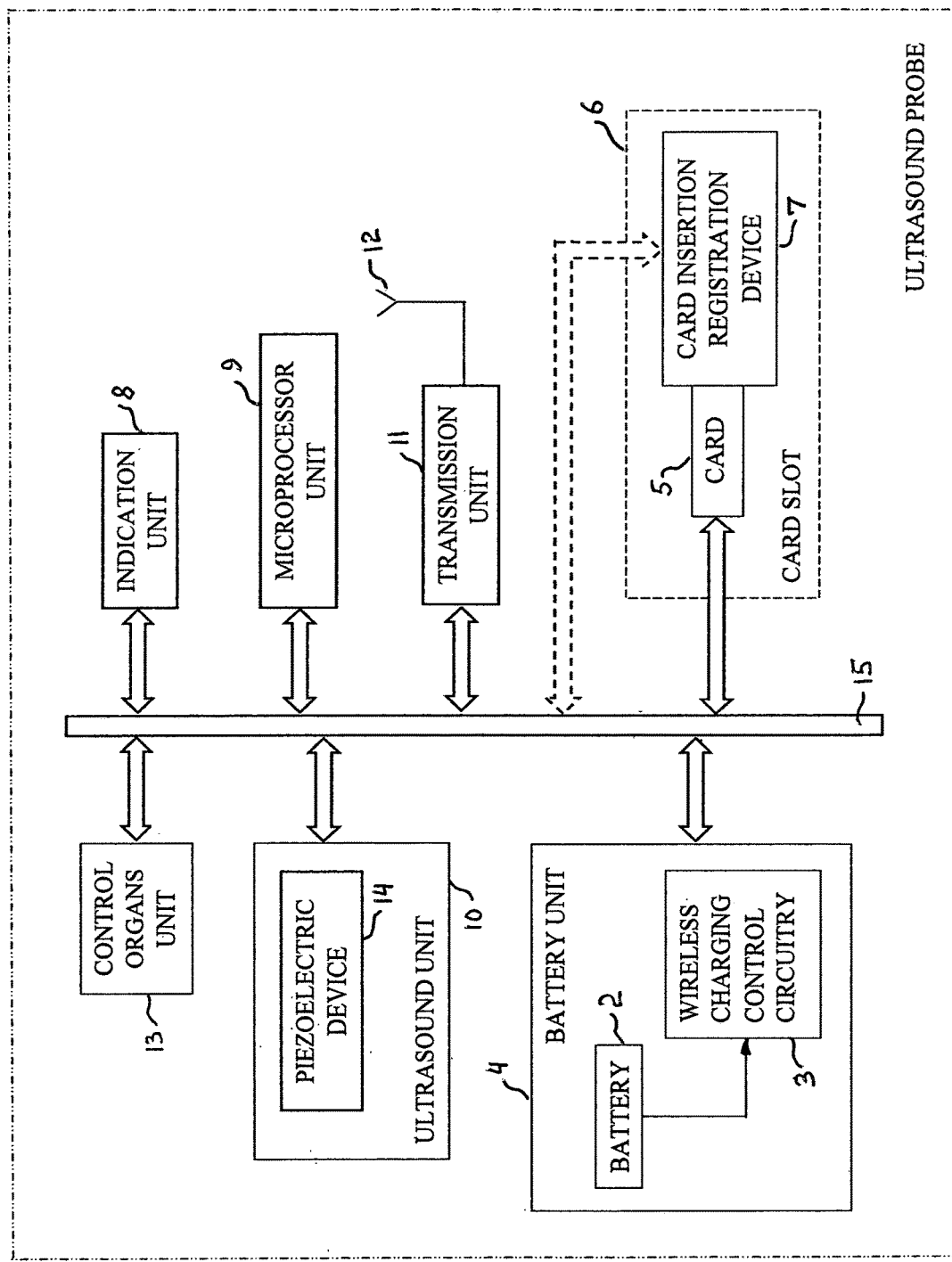
FIG. 2 is a simplified drawing (block-diagram) of the improved ultrasound probe with the multiplexed bus.

As demonstrated in FIGS. 1 and 2, the battery unit 4 provides a power supply line 17 connected to all units of the probe 1 and to the card (removable memory card) 5, which can be inserted in the card slot 6 located in any reasonably convenient place (not shown) of the probe 1. When the card 5 is inserted in the slot 6, the card insertion registration device 7 [which can be represented by a single or a plurality of sprang contacts (not shown) or by a push-button mini/micro switch (not shown), etc.] produces a signal indicating the insertion and use of the probe's removable memory card 5. This signal by ninth control (indication) line 55 follows to the indication unit 8. When the card insertion registration device 7 comprises the electrical element(s), for example, such as electrical relay [not shown], etc., then the power supply line 17 from battery unit 4 can be connected to the card insertion registration device 7 too, as it is shown in FIGS. 1 and 2. The card insertion registration device 7 connected by control line 55 to the indication unit 8, which is connected to the microprocessor unit 9. It should be understandable, that the title of the microprocessor unit 9 is not limited to the microprocessor only. It can be any appropriate type of controller, CPU (Central Processing Unit), etc., still teaching of the improved method(s) and apparatus of the present invention.

The microprocessor unit 9 is connected to the card 5, to ultrasound unit 10 and to transmission unit 11, which is connected to antenna 12. Also, the microprocessor unit 9 is connected to control organs unit 13. The control organs unit 13 is connected to ultrasound unit 10, comprising the piezoelectric device 14.

It is known, that intensity of ultrasound depends on high frequency of ultrasound [sometimes, intensity can be correlated with the length of wave "X" (not involved hereinbelow)].

Therefore:

$$I = \mu C V_m^2 / 2 \qquad (1)$$

wherein: I—intensity of ultrasound; μ—a density of the material/environment (e.g., density of human body, etc.); C—ultrasound's velocity inside of the environment; $V_m$—maximal amplitude of the velocity.

At the same time, it is known that:

$$V_m = 2\pi F Y_m \qquad (2)$$

wherein: F—frequency of oscillation; $Y_m$—amplitude of oscillation.

Then, according to (1) and (2), the intensity would be:

$$I = 2\pi^2 \mu C Y_m^2 F^2 \qquad (3)$$

Thus, the intensity "I" can be described by the following equation:

$$I = f\{F, Y_m, C, \mu\} \qquad (4)$$

wherein: ƒ—functional (symbol of function).

Also, the control organs unit 13 is connected to indication unit 8 and to battery unit 4, which provides the signal(s) to indication unit 8 and control organs unit 13 by the control/indication lines, shown in FIGS. 1 and 2, wherein FIG. 2 illustrates the communication of the probe's units with each other via multiplexed bus 15.

The improved methods provide the following operation of the improved wirelessly chargeable ultrasound probe with the record of the ultrasound data/images on the removable memory card.

Referring to FIG. 1, the battery unit 4 can comprise a battery 2 of different kinds: regular (non-chargeable, replaceable) battery [shown in FIGS. 1 and 2 as a battery 2] or chargeable by cable battery (battery chargeable by cable) [shown in FIGS. 1 and 2 as a battery 2] or wirelessly chargeable battery [shown in FIGS. 1 and 2 as a battery 2]. The battery 2 is connected to the wireless charging control circuitry 3. Depending on the battery type, the operator of the ultrasound probe 1 selects on the control organs unit 13 the appropriate type of battery 2, used for the probe 1 [the selection can be provided by pushing of the appropriate push-button switch (not shown) on the ultrasound probe 1 or selecting the appropriate position on the multi-position switch (not shown) or on push-button control panel (not shown), etc.] The first control signal from control organs unit 13 by first control line 16, as it is shown in FIG. 1, follows to the battery unit 4, wherein connects the regular battery [which is non-chargeable, but replaceable battery] through the circuitry 3 to the power supply line 17 (if the regular battery in use), or, if the chargeable by cable battery in use, the second control signal from control organs unit 13 by first control line 16 connects the chargeable battery [which is charged by the cable (not shown)] to the power supply line 17 through the circuitry 3, or, if the wirelessly chargeable battery is used, the third control signal from control organs unit 13 by first control line 16 connects the wirelessly chargeable battery to the power supply line 17 through the circuitry 3.

Figure 3:
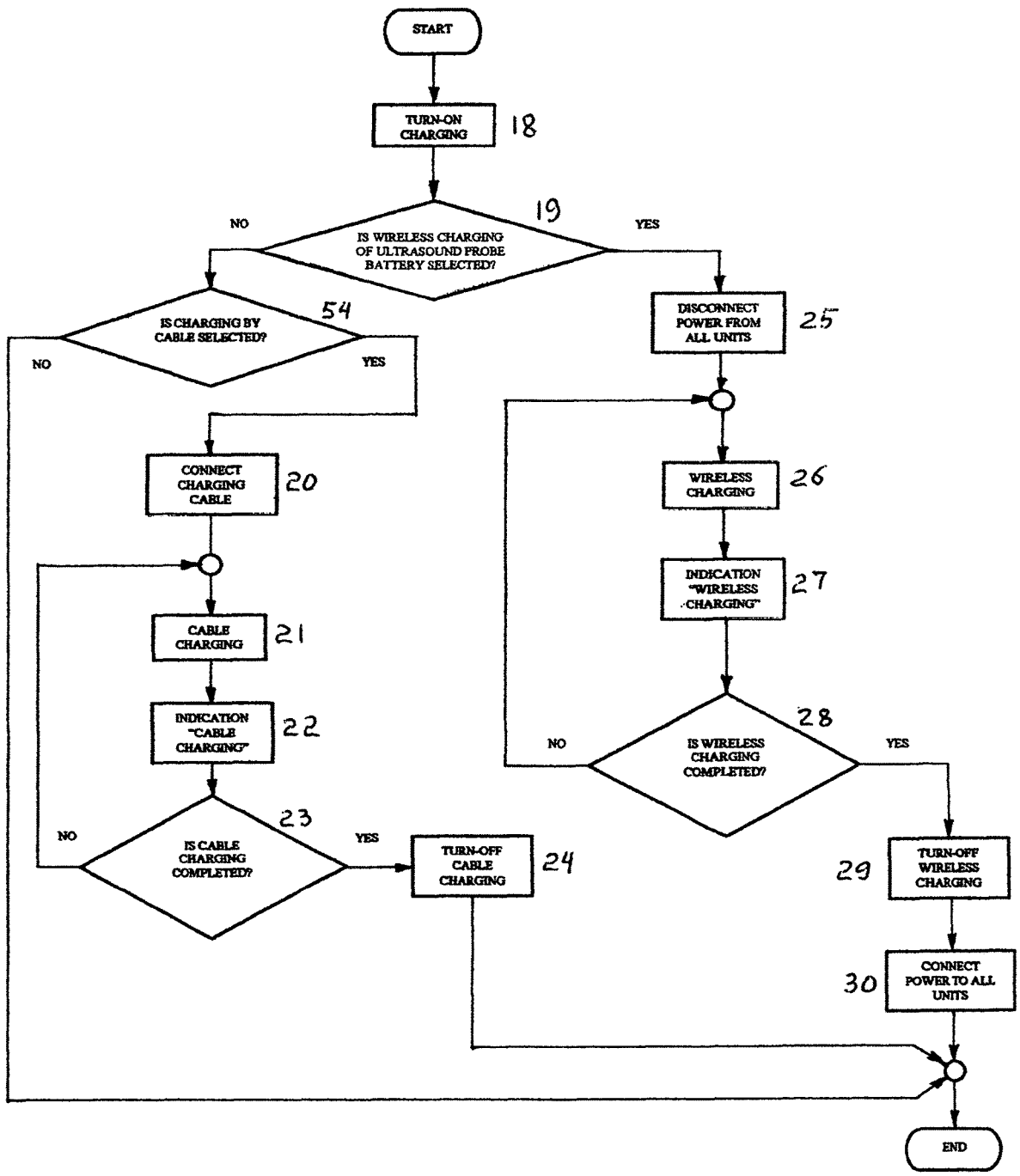
FIG. 3 is a simplified flowchart (algorithm) illustrating the operation of the improved ultrasound apparatus (probe) during battery charging.

As it is described hereinabove and below, the ultrasound probe chargeable (rechargeable) battery can be charged by the cable (not shown in FIG. 1), as it is illustrated in FIG. 3 [predicates 19, 54, 23 and blocks 18, 20-22, 24, 30]. The ultrasound probe wirelessly chargeable battery can be charged wirelessly, as it is also illustrated in FIG. 3. If the wirelessly chargeable battery in use, the power supply line 17 is disconnected (by circuitry 3 when the third control signal from control organs unit 13 is presented in the first control line 16) from all units/device(s)/card of the probe 1 during charging period, as it is shown in FIG. 3 [predicates 19, 28 and blocks 18, 25-27, 29, 30]. The type of the selected battery 2 is indicated [e.g., by LED/Light Emitting Diode/ (not shown) or on the mini display (not shown), etc.] in the indication unit 8 of the probe 1 by the signal on the second control (indication) line 31. For instance, the indicators (e.g., LED/not shown/) can be of the different color, i.e.: for example LED (not shown) indicating a wireless charging 27 (see FIG. 3) can be green, LED (not shown) indicating a cable charging 22 (see FIG. 3) can be blue, LED (not shown) indicating the presence of the regular non-chargeable battery can be yellow (the indication of presence of the regular non-chargeable battery is not shown in FIG. 3, but for example, could be presented in FIG. 3 by the algorithm's block "indication 'regular battery'" located between predicate 54 ("NO") and block "END"). Another example: the algorithm in FIG. 3 conditionally does not require the disconnection of the power from all units if the charging by cable battery is selected, but if the charging instruction requires such disconnection during charging procedure, then the algorithm in FIG. 3 can comprise such blocks (e.g., analogously to the blocks 25, 30/FIG. 3/) which are not shown in FIG. 3 but could be presented in FIG. 3 between blocks 54 and 20, and between blocks 24 and block "END" respectively. Also, the type of indication can be different too, for example, the "low battery" indicator (e.g., LED/not shown/) can blink, "charge completed" indicator (e.g., LED/ not shown/) can be in the "turned-on" position without blinking, etc. The analogous principles of indication(s) and indicator(s) can be applicable, for example, to the indication of "probe card inserted" 44 (see FIG. 4) or "phone card inserted" 42 (see FIG. 4), etc. It is clearly understandable, that all drawings/flowcharts are presented in the simplified manner and are not limited to the depicted components (e.g., units/circuitries/card(s)/blocks/predicates, etc.), still teaching of the improved methods and ultrasound apparatus of the present invention.

Figure 4:
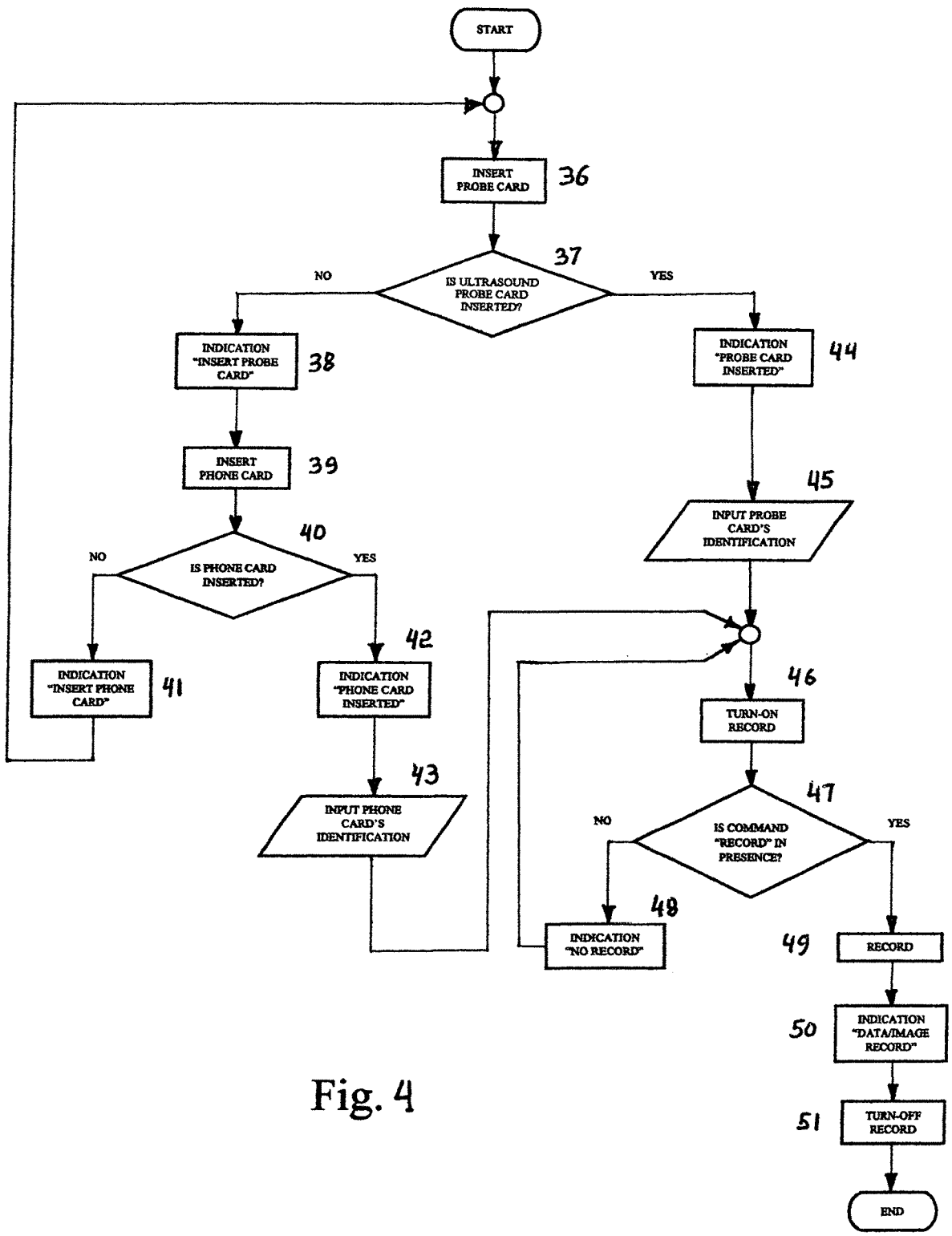
FIG. 4 is a simplified flowchart (algorithm) illustrating the operation of the improved ultrasound apparatus (probe) with removable memory card.

Referring to FIG. 4, illustrating the operation of the ultrasound probe 1 with respect to the removable memory card 5, the simplified general operation includes the initial step which is an insertion of the card 5 in the slot 6 of the probe 1 or in the Smart Device (e.g. such as Smart Phone, iPad, iPhone, etc.). The selection is provided in control organs unit 13, by pushing appropriate push-button switch (not shown) or positioning multi-position switch (not shown) in the appropriate position, etc. The fourth control signal from control organs unit 13 by third control line 32, as it is shown in FIG. 1, follows to the microprocessor unit 9 for initiation of processing procedures, etc. Also, the appropriate exchange of information/data and control data/ commands (e.g., in the digital form) is provided between microprocessor unit 9 and removable memory card 5, ultrasound unit 10, transmission unit 11 and indication unit 8, as it is shown in FIG. 1 (the FIG. 2 illustrates the complete digital communication, for example by the multiplexed bus 15, within the ultrasound probe 1).

The control signals also follow by the fourth control line 33 from the control organs unit 13 to the indication unit 8 for control of the electronics [e.g., relays, transistors, triggers, etc. (not shown)] of the indication unit 8. The controlling signal(s) (e.g., such as ultrasound image recordation condition/stage, etc.) from microprocessor unit 9 follow by fifth control line 34 to the control organs unit 13. Additionally, the control signals (e.g., alarmed condition of the battery or presence of the charging process, etc.) from wireless charging control circuitry 3 of battery unit 4 follow by the six control line 35 to the control organs unit 13. The control of the ultrasound unit 10 is provided by the seventh control line 52, and the appropriate responses (e.g., "start/end diagnosis", etc.) can follow by the eighth control line 53 to the control organs unit 13 for further controlling procedures.

It should be understandable, that the quantity of the control lines and their functional meaning are presented conditionally in the FIG. 1 for more specific and full description of the signals' functional purposes. The control signals (control lines) can be represented by an electrical cable (not shown) or can be represented by a single digital control line (not shown), or by an additional multiplexed bus (not shown) or by the same multiplexed bus 15, as for example, shown in FIG. 2, etc. The presentation of the signal/data lines in FIGS. 1 and 2 are not limited to the described in this invention and can be reasonably equivalently inter-distributed (inter-re-distributed) between the units/device(s)/circuitries/card, still teaching of the improved methods and ultrasound apparatus of the present invention.

Additionally, the control of the ultrasound unit 10 and piezoelectric device 14 can be provided by the control organs unit 13 via microprocessor unit 9, and vice versa. The microprocessor unit 9 also can provide the initial processing of ultrasound information/data and ultrasound images with transmission through the transmission unit 11 and antenna 12 to the central station (not shown) for complete processing of the ultrasound images and displaying them on the display/monitor (not shown) of the central station (not shown), or can provide the full processing of ultrasound information/data and ultrasound images with transmission them to the Smart Device (e.g., Smart Phone, iPad, iPhone, etc.). It should be understandable, that the transmission of ultrasound information/data and images, processed in the improved probe, to the Smart Device can be provided by the cable instead of the wireless transmission, but it still continue teaching of the improved methods and apparatus of the present invention.

It is also understood, that the ultrasound unit 10 can comprise its own additional microprocessor device/unit (not shown) or any other controller (not shown), etc., and the processing of the ultrasound information/data/images can be provided by either one of them or both of them.

Also, it is still should be understandable, that some units/circuitries/card(s)/blocks, etc. can be included in the central station (not shown), but it will still continue teaching of this invention.

The operations with the probe's removable memory card 5 or Smart Device's removable memory card (not shown) are presented in FIG. 4. The operations with the probe's card 5 are described by the predicates 37, 47 and blocks 36, 44-46, 48-51, and operations with the Smart Device's card are described by the predicates 37, 40, 47 and blocks 36, 38, 39, 41-43, 46, 48-51.

As it was described hereinabove, when the card 5 is inserted in the slot 6, the card insertion registration device 7 [which can be represented by a pair of sprang contacts (not shown) or by a push-button mini/micro switch (not shown)] produces a signal indicating the insertion and use of the probe's removable memory card 5. When the card insertion registration device 7 comprises the electrical element(s), for example, such as electrical relay [not shown], etc., then the power supply line 17 from battery unit 4 can be connected to the card insertion registration device 7, as it is shown in FIGS. 1 and 2. If the Smart Device's card is used, the signal of the presence of the card in the Smart Device is wirelessly (or by cable) transmitted to the ultrasound probe 1. With the wireless transmission, the received signal follows (via probe's transmission unit 11 and microprocessor unit 9) to the indication unit 8, where is illuminated by the appropriate LED (not shown) or, for example, appears on the probe's mini display (not shown), etc.

It should be understandable, that the structures and functions of the units/devices/card/circuitry presented in FIGS. 1-4 are not limited to the described in this invention and can be reasonably equivalently inter-distributed (inter-re-distributed) between each other, still teaching of the improved apparatus of the present invention. Also, it is understood that exemplification of the improved structures and steps of the methods are simplified and presented conditionally, and may be represented by any similar structures and steps, continuing teaching of the improved methods and apparatus of the present invention.

The improved methods and ultrasound apparatus with the wirelessly chargeable battery of the ultrasound probe and with the record of the ultrasound data/images on the removable memory card are significantly needed to provide the ultrasound diagnosis independently from the length of electrical cables and/or from the necessity of the A/C power source presence, and independently from the patient location (e.g. emergency patients in the wild mountain forests areas, in the rural Alaskan or other difficult to approach areas, etc.), etc.

CONCLUSION, RAMIFICATION AND SCOPE

Accordingly the reader will see that, according to the invention, the improved methods and ultrasound apparatus with the wirelessly chargeable battery of the ultrasound probe and with the record of the ultrasound data/images on the removable memory card are provided. There has thus been outlined, rather broadly, the more important features of the invention. In this respect, it is understood that the invention is not limited in its application to the details of steps, construction/structures and to the arrangements of the components (units/devices, etc.) set forth in the description and/or drawings. The invention is capable of other embodiments and of being practiced and carried out in various ways. Also, it is to be understood that the phraseology and terminology employed herein are for the purpose of description and should not be regarded as limiting.

While the above description contains many specificities, these should not be construed as limitations on the scope of the invention, but as exemplification of the presently-preferred embodiments thereof. Many other ramifications are possible within the teaching to the invention. For instance, the improved methods and structure(s) can be fully and successfully used in the biology science for research of the specific tissues by ultrasound probes, etc.

The persons of ordinary skills and/or creativity in the art will readily observe that numerous modifications and advantages of the improved methods and ultrasound probe may be made while retaining the teachings of the invention.

As such, those skilled in the art will appreciate that the conception, upon which this disclosure is based, can readily be utilized as a basis for the designing of other ultrasound probes, for carrying out the several purpose of the present invention. It is important, therefore, that the claims be regarded as including such equivalent constructions insofar as they do not depart from the spirit and scope of the present invention.

THE DRAWING REFERENCE NUMERALS

1.—an ultrasound probe;
2.—a battery;
3.—a wireless charging control circuitry;
4.—a battery unit;
5.—a removable memory card;
6.—a removable memory card's slot;
7.—a card insertion registration device;
8.—an indication unit;
9.—a microprocessor unit;
10.—an ultrasound unit;
11.—a transmission unit;
12.—an antenna;
13.—a control organs unit;
14.—a piezoelectric device;
15.—a multiplexed bus;
16.—a first control line;
17.—a power supply line;
18, 20-22, 24, 25-27, 29, 30—the algorithm's blocks (FIG. 3);
19, 23, 28—algorithm's predicates (FIG. 3);
31.—a second control line;
32.—a third control line;
33.—a fourth control line;
34.—a fifth control line;
35.—a sixth control line;
36, 38, 39, 41-46, 48-51—the algorithm's blocks (FIG. 4);
37, 40, 47—algorithm's predicates (FIG. 4);
52.—a seventh control line;
53.—an eighth control line;
54.—algorithm's predicate (FIG. 3);
55.—a ninth control line.

What is claimed is:

1. A method for selection and control of a power supply of an ultrasound probe comprising steps of:

selecting, by an operator, said power supply from a non-chargeable battery or a chargeable battery by a wire or wires or a wirelessly chargeable battery for a use in said ultrasound probe, wherein the operator selects said power supply using a control organs unit;

providing a first control signal from the control organs unit of said ultrasound probe to a battery unit, comprising said non-chargeable battery, wherein said first control signal provides a connection of a power supply line from said non-chargeable battery to said control organs unit, to said microprocessor unit, to a transmission unit including an antenna, to a card slot including a card and a card insertion registration device, to an ultrasound unit including a piezoelectric device, and to an indication unit controlled by said control organs unit or by said microprocessor unit of said ultrasound probe by said battery unit, and wherein said non-chargeable battery is selected for said use in said ultrasound probe;

providing a second control signal from said control organs unit or from said microprocessor unit of said ultrasound probe to said battery unit, comprising said chargeable battery by said wire or said wires, wherein said second control signal provides a connection of a power supply line from said chargeable battery to said control organs unit, to said microprocessor unit, to said transmission unit including said antenna, to said card slot including said card and said card insertion registration device, to said ultrasound unit including said piezoelectric device, and to said indication unit of said ultrasound probe by said battery unit before a charging cycle of said chargeable battery by said wire or said wires, and wherein said chargeable battery by said wire or said wires is selected for said use in said ultrasound probe;

providing a third control signal from said control organs unit or a microprocessor unit of said ultrasound probe to said battery unit, comprising said wirelessly chargeable battery, wherein said third control signal provides a connection of a power supply line from said wirelessly chargeable battery to said control organs unit, to said microprocessor unit, to said transmission unit including said antenna, to said card slot including said card and said card insertion registration device, to said ultrasound unit including said piezoelectric device, and to said indication unit of said ultrasound probe by said battery unit before a charging cycle of said wirelessly chargeable battery, and wherein said wirelessly chargeable battery is selected for said use in said ultrasound probe;

providing an indication of said charging cycle of said chargeable battery by said wire or said wires or said charging cycle of said wirelessly chargeable battery of said battery unit of said ultrasound probe in said indication unit of said ultrasound probe.

2. The method of claim 1, wherein further said second control signal provides a disconnection of said chargeable battery from said control organs unit, from said microprocessor unit, from said transmission unit including said antenna, from said card slot including said card and said card insertion registration device, from said ultrasound unit including said piezoelectric device, and from said indication unit of said ultrasound probe by said battery unit of said ultrasound probe before said charging cycle of said chargeable battery, and provides said connection of said chargeable battery to said control organs unit, to said microprocessor unit, to said transmission unit including said antenna, to said card slot including said card and said card insertion registration device, to said ultrasound unit including said piezoelectric device, and to said indication unit of said ultrasound probe by said battery unit after a completion of said charging cycle of said chargeable battery, and wherein a charging instruction requires said disconnection of said chargeable battery from said control organs unit, from said microprocessor unit, from said transmission unit including said antenna, from said card slot including said card and said card insertion registration device, from said ultrasound unit including said piezoelectric device, and from said indication unit of said ultrasound probe before said charging cycle.

3. The method of claim 1, wherein further said third control signal provides a disconnection of said wirelessly chargeable battery from said control organs unit, from said microprocessor unit, from said transmission unit including said antenna, from said card slot including said card and said card insertion registration device, from said ultrasound unit including said piezoelectric device, and from said indication unit of said ultrasound probe by said battery unit of said ultrasound probe before said charging cycle of said wirelessly chargeable battery, and provides said connection of said wirelessly chargeable battery to said control organs unit, to said microprocessor unit, to said transmission unit including said antenna, to said card slot including said card and said card insertion registration device, to said ultrasound unit including said piezoelectric device, and to said indication unit of said ultrasound probe by said battery unit after a completion of said charging cycle of said wirelessly chargeable battery, and wherein a charging instruction requires said disconnection of said wirelessly chargeable battery from said control organs unit, from said microprocessor unit, from said transmission unit including said antenna, from said card slot including said card and said card insertion registration device, from said ultrasound unit including said piezoelectric device, and from said indication unit of said ultrasound probe before said charging cycle.

4. An ultrasound apparatus comprising:
  a central ultrasound station or a Smart Device, wherein said central ultrasound station or said Smart Device comprises a display;
  an ultrasound probe comprising:
    an ultrasound unit including a piezoelectric device with ultrasound transducers to transmit an ultrasound wave to a subject and receive a reflection wave from the subject;
    a microprocessor unit connected to the ultrasound unit for processing of ultrasound data and ultrasound images, wherein said ultrasound data and said ultrasound images are provided by an ultrasound intensity $I=f\{F,Y_m,C,\mu\}$, wherein I—said intensity of the reflected ultrasound wave, $Y_m$-an amplitude of oscillation, C—a velocity of said ultrasound inside of an environment, and $\mu$-a density of said environment;
    a card slot for insertion of a removable memory card providing a recordation of the ultrasound data and ultrasound images, wherein said card slot includes said removable memory card and a card insertion registration device wherein said microprocessor unit is connected to said removable memory card and to a transmission unit which is connected to an antenna, wherein said transmission unit of said ultrasound probe transmits said ultrasound data and said ultrasound images to said central ultrasound station or to said Smart Device wirelessly, and wherein said ultrasound data and said ultrasound images are displayed on said display;
    an indication unit connected to said microprocessor unit;
    a control organs unit connected to said microprocessor unit, to said indication unit, and to said ultrasound unit including said piezoelectric device;
    a battery unit including a non-chargeable battery or a chargeable battery by a wire or wires or a wirelessly chargeable battery including a wireless charging control circuitry connected to said non-chargeable battery or to said chargeable battery or to said wirelessly chargeable battery, wherein said battery unit provides a power supply line to said removable memory card, to said microprocessor unit, to said transmission unit, to said indication unit, to said ultrasound unit, and to said control organs unit, and wherein said wireless charging control circuitry controls a charge of said chargeable battery or controls said charge of said wirelessly chargeable battery and controls a disconnection and a connection of said power supply line to said microprocessor unit, said indication unit, said transmission unit, said removable memory card, said control organs unit and to said ultrasound unit, and wherein a charging instruction requires said disconnection of said chargeable battery or said disconnection of said wirelessly chargeable battery from said control organs unit, from said microprocessor unit, from said transmission unit including said antenna, from said card slot including said card and said card insertion registration device, from said ultrasound unit including said piezoelectric device, and from said indication unit of said ultrasound probe before a charging cycle, and wherein said control organs unit is configured to select said power supply from said non-chargeable battery or said chargeable battery or said wirelessly chargeable battery.

5. The ultrasound apparatus of claim 4, wherein further said Smart Device is a Smart Phone or an iPad or an iPhone.

6. The ultrasound apparatus of claim 4, wherein further said transmission unit of said wirelessly chargeable ultrasound probe transmits said ultrasound data and said ultrasound image to said central ultrasound station or to said Smart Device by a said wire or said wires.

7. The ultrasound apparatus of claim 6, wherein further said wire or said wires is an electrical cable.

8. The ultrasound apparatus of claim 4, wherein further said card insertion registration device is connected to said power supply line.

9. The ultrasound apparatus of claim 4, wherein further said microprocessor unit, said indication unit, said transmission unit, said removable memory card, said control organs unit, said battery unit and said ultrasound unit are connected to each other by a multiplexed bus for a communication.

10. The ultrasound apparatus of claim 9, wherein further said microprocessor unit, said indication unit, said transmission unit, said removable memory card, said control organs unit, said battery unit and said ultrasound unit are connected by said multiplexed bus to said card insertion registration device for said communication.

* * * * *